United States Patent
Braun et al.

(10) Patent No.: US 6,489,510 B1
(45) Date of Patent: Dec. 3, 2002

(54) PRODUCTION OF CARBOXYLIC ACID FLUORIDES

(75) Inventors: Max Braun, Wedemark (DE); Kerstin Eichholz, Langenhagen (DE); Werner Rudolph, Hannover (DE)

(73) Assignee: Solvay Fluor und Derivate GmbH, Hannover (DE)

( * ) Notice: Subject to any disclaimer, the term of this patent is extended or adjusted under 35 U.S.C. 154(b) by 0 days.

(21) Appl. No.: 09/319,451

(22) PCT Filed: Nov. 28, 1997

(86) PCT No.: PCT/EP97/06647

§ 371 (c)(1),
(2), (4) Date: Jul. 29, 1999

(87) PCT Pub. No.: WO98/24750

PCT Pub. Date: Jun. 11, 1998

(30) Foreign Application Priority Data

Dec. 4, 1996 (DE) ......................................... 196 50 212

(51) Int. Cl.$^7$ .............................................. C07C 53/38

(52) U.S. Cl. ...................................................... 562/849

(58) Field of Search ......................................... 562/849

(56) References Cited

FOREIGN PATENT DOCUMENTS

| EP | 668261 A1 | 8/1995 |
|----|-----------|--------|
| WO | WO 88 04281 | 6/1988 |
| WO | WO 91/09673 | 7/1991 |
| WO | WO 95/09815 | 4/1995 |

*Primary Examiner*—Paul J. Killos
(74) *Attorney, Agent, or Firm*—Crowell & Moring LLP

(57) ABSTRACT

A method for producing carboxylic acid fluorides of the formula RCFXC(O)F, where X represents fluorine or chlorine, in good yields and with good selectivity for the carboxylic acid fluorides by reacting compounds of the formula RCFXCHFCl with oxygen by photochemical oxidation in the gaseous phase, preferably under sensitization with chlorine and using light having a wavelength $\lambda \geq 280$ nm, which conditions make it possible to work without the use of pressure. Glass apparatus may be covered with a protective coating so as to protect it against traces of hydrogen fluoride. To this end, for example, heat-shrinkable sleeves made of light-permeable hydrogen fluoride-resistant material may be used. Polytetrafluoroethylene, polyfluoropropylene or a mixture thereof are especially suitable for this purpose. This type of protection is also suitable for other reactions such as photo-induced fluoro-dediazonation in hydrogen fluoride/pyridine for the production of aromatic compounds fluorinated in the nucleus or the oxidation of $CHCl_2$ groups for the production of carboxylic acid chlorides.

18 Claims, No Drawings

PRODUCTION OF CARBOXYLIC ACID FLUORIDES

BACKGROUND OF THE INVENTION

The invention relates to a process for the production of carboxylic acid fluorides by photochemical oxidation and to an apparatus therefor.

Polyhalogenated carboxylic acid fluorides are intermediates in chemical synthesis. They can be used, for example, in the production of water-repellant or oil-repellant compounds for use in paper and cloth. They can also be used as a precursor for the production of surface active substances or in flameproofing.

Perfluorocarboxylic acid fluorides can be prepared according to European Patent Application EP-A 260713 by the heat treatment of perfluoroalkyl vinyl ethers in the presence of special salts containing fluorides, such as alkali fluorides, alkaline earth fluorides, fluorometallates, transition metal fluorides or oxyfluorides. A minimum temperature of 250° C. is necessary for the heat treatment. Conversion rates and selectivity are not constant throughout the course of the reaction: initially the conversion rates and the selectivity are low.

International Patent Application WO 96/29298 entitled: "Process for the production of polyfluoracyl preparations" discloses that polyhaloacyl fluorides such as trifluoroacetyl fluoride and difluoroacetyl fluoride can be produced by oxidation of 1-chloro-1,2,2,2-tetrafluoroethane or 1,1-dichloro-2,2-difluoroethane. This is a thermal process which is performed as regards temperature and pressure at or above the critical point. The process is not very selective regarding the formation of carboxylic acid fluoride: in the production of trifluoracyl compounds, trifluoroacetyl fluoride forms in an amount of at least 60 to 70 mole-%, trifluoroacetyl chloride in an amount from 5 to 15 mole-%, trifluoroacetic acid in an amount of 10 to 20 mole-%, 5 to 10 mole-% of a dimerization product (octafluorodichlorobutane), and 1 to 5 mole-% of chlorofluorophosgene.

SUMMARY OF THE INVENTION

The object of the present invention is to provide a method whereby carboxylic acid fluorides can be produced in a technical simple manner in a high yield and with a high selectivity. This object is achieved by the method of the invention.

The method of the invention for preparing carboxylic acid fluorides of the general formula RCFXC(O)F comprises the photochemical oxidation of compounds of the general formula RCFXCHFCl as an educt, in which R represents F or linear perfluorinated C1–C9 alkyl or branched, perfluorinated C1–C9 alkyl, and X represents chlorine or fluorine, with oxygen as reactant in the gas phase. The operation is thus carried out with activating irradiation of the gaseous reaction mixture. The irradiation can be carried out through glass of any composition (e.g., through glass within the apparatus, glass enclosures for the irradiator). For example, quartz glass apparatus can be used. The rate of reaction is increased when it is performed in the presence of a sensitizer, especially in the presence of elemental chlorine as sensitizer. Irradiators such as radiation lamps and fluorescent tubes can be used, which emit radiation within a range of 200 to 600 nm, for example. It is advantageous to perform an activating irradiation with light of a wavelength of $\lambda \geq 280$ nm. The invention will be further explained with reference to this preferred embodiment.

DESCRIPTION OF THE PREFERRED EMBODIMENTS

Conversion rates, yield and selectivity are especially high if the reaction is performed in the presence of elemental chlorine and selects an activating irradiation with light having a wavelength of $\lambda \geq 280$ nm. Frequencies of a wavelength below 280 nm are then substantially masked out of the frequency spectrum. This can be done by using lamps which emit only light of a wavelength above or at 280 nm, and/or by using means which mask out the corresponding frequencies from the emitted light. For example, radiation can be performed through glass which is permeable only for light of a wavelength of 280 nm or above, i.e., glass which filters out the shorter-wavelength content of the radiation. Borosilicate glasses, for example, are well suited for the freqpurpose. Suitable glasses contain, for example, 7 to 13% $B_2O_3$, 70 to 80% $SiO_2$, also 2 to 7% $Al_2O_3$ and 4 to 8% $Na_2O+K_2O$ as well as 0 to 5% alkaline earth metal oxides (all weight-percent). Known brand names for borosilicate glass e s are Duran, Pyrex and Solidex.

Particularly well suited for the irradiation are lamps which emit only (UV) light of a wavelength above or at 280 nm. Especially fluorescent tubes (e.g., those made by Philips) are very well suited. With such lamps the irradiation can be performed through quartz glass, but also through the glasses described above which filter out the shorter wavelength component of the radiation. It is of course necessary that the lamps or tubes emit also in the absorption range of elemental chlorine. In addition to the especially suitable fluorescent tubes, radiation lamps (e.g., medium or high-pressure mercury lamps) can also be used, for example; any lines in the range below 280 nm are filtered out, for example by radiating through a glass which is permeable only to light having a wavelength at or above 280 nm. Usable glasses are described further above. Also well suited for the irradiation are lamps, e.g., mercury high-pressure lamps, which radiate mainly or only in the preferred wavelength range at or above 280 nm on account of a dopant. High-pressure mercury lamps, for example, exhibit a quite intense band in the range of 254 nm, which, as described above, can be filtered out through borosilicate glass, for example. In the case of high-pressure mercury lamps doped with metal iodides, this line is greatly suppressed. The often over-proportional increase of the conversion rate when such doped radiators are used is surprising. Especially well suited are high-pressure mercury lamps which are doped with gallium iodide, especially thallium iodide or cadmium iodide. Even when such doped lamps are used, it is advantageous to filter out the shorter wavelength radiation component with $\lambda<280$ nm, for example by working in borosilicate glass.

With regard to reaction temperature and pressure it is possible to conduct the reaction so that no condensation occurs within the photoreactor. If higher boiling educts are used, it can be performed in vacuo, for example. In regard to temperature, the reaction is advantageously carried out at temperatures up to 200° C. The preferred temperature range is 30 to 150° C. As stated, the operation can be performed at reduced pressure; preferably the pressure is at least 1 bar absolute. It is especially preferred to operate at a pressure of 1 to 10 bar (abs.). It is very especially preferred to operate in a pressureless manner. The term, "pressureless," in the context of the present invention, means that no additional pressure acts upon the reaction mixture except for the ambient pressure (i.e., about 1 bar), the oxygen gas pumping pressure (or that of an oxygen-containing gas, since air or mixtures of oxygen and inert gas, for example, can be used) and the optionally utilized chlorine as well as the pressure that may develop due to hydrogen chloride gas forming in the reaction. The total pressure in the reactor then is advantageously lower than 2 bar absolute or, depending on the pumping pressure, even lower than 1.5 bar absolute, but greater than the ambient pressure.

The process can be performed batch-wise or continuously, in which case the reaction is advantageously carried out in a continuous-flow apparatus. Preferably, one proceeds by continuously feeding starting material (the corresponding educt, oxygen or an oxygen-containing gas, and, optionally chlorine) into the continuous-flow apparatus and continuously withdrawing reaction product in an amount corresponding to the amount fed in.

The molar ratio between the educt and oxygen can vary within a wide range; however, it is desirable to use at least 0.4 mole of oxygen per mole of starting compound. Especially good results are achieved if the molar ratio between the starting compound and the oxygen ranges from 1:0.4 to 1:1, especially 1:0.4 to 1:0.6. The oxygen can be used, as stated, in the form of air, as a mixture of $O_2$ and insert gas, but preferably as pure oxygen. If the irradiation is performed in the presence of chlorine as sensitizer, the molar ratio between the educt and the elemental chlorine can also vary within a wide range, e.g., 1:0.01 to 1:1. Especially good results are achieved if the molar ratio between the educt and the elemental chlorine lies in the range from 1:0.05 to 1:0.2.

In regard to purity of the product it is desirable that as little water as possible be present during the reaction (for example, less than 30 ppm). If desired, the reactants can be freed of entrained water in a known manner, e.g., by means of a molecular sieve.

The average residence in the reaction vessel is advantageously between 0.01 and 30 minutes, preferably 4 between 0.5 and 3.5 minutes. The optimum average residence, time, which depends on, among other things, the type of lamps, the radiation power of the lamps and on geometric parameters of the irradiation apparatus, can be determined by simple manual tests and analysis of the product stream, for example by gas chromatography. It may also be advantageous to agitate the reaction mixture in the reactor, for example by means of suitable built-in devices. No fluid coolant needs to be added to the reaction mixture.

Preferred educts to which the process of the invention is applied are those in which R represents fluorine or linear, perfluorinated C1 to C4 alkyl or branched perfluorinated C1–C4 alkyl. Especially, educts are used in which R represents fluorine, $CF_3$ or $CF_3CF_2$. In particular, the following carboxylic acid fluorides can be produced:

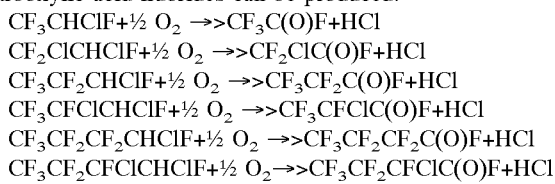

To protect the surface of the glass apparatus it can be modified to guard it against attack by the HCl gas and any traces of HF that might form. For this purpose, for example, transparent films or "socks" can be drawn over the surfaces to be protected. Suitable materials include poly- or perfluorinated synthetic resins such as polytetrafluoro-ethylene (PTFE), perfluoropolypropylene (FEP), perfluoroalkoxy polymers (PFA) or polyvinylidene difluoride (PVDF) and mixtures thereof.

The method has the advantage over the known method of producing carboxylic acid fluorides that it can be performed with a high conversion rate and high selectivity at low temperatures. It is therefore very effective. Furthermore, it can be performed at low pressure, if desired.

The invention also relates to an irradiating apparatus which can be used in the process of the invention and is specially modified. Irradiating apparatus usually have a container for a liquid, gas or gas mixture to be irradiated, as well as a casing in which the irradiator is held. Often such apparatus have a shaft in which the irradiator is arranged (immersion shaft reactors). Known are radiation apparatus of glass, e.g., quartz glass or borosilicate glass, with a glass casing. The irradiation apparatus of the invention has a container for receiving a gas to be irradiated and an irradiator which is arranged in a casing which is in contact with the gas to be irradiated, wherein at least a portion of the surface of the container in contact with the gas to be irradiated having a protective covering permeable to the radiation, insofar as the casing, particularly an immersion shaft, is made of glass. Alternatively, the immersion shaft, the casing or the entire apparatus can be made of radiation-permeable (i.e., light-permeable) polymer, preferably of polyfluorinated or perfluorinated polymer, such as PTFE, FEP, PFA, PVDF, or mixtures thereof. Preferred protective coverings are named above, e.g., those of polytetrafluoroethylene (PTFE), FEP or mixtures thereof. Especially preferred are irradiation apparatus according to the invention, which have a protective covering in the form of a shrink tubing of PTFE or PTFE-FEP, which is drawn onto the glass casing of the radiator. The radiation apparatus according to the invention are especially immersion shaft reactors, wherein the protective covering (preferably a PTFE or PTFE-FEP shrink tubing) is applied to the cooling finger of the immersion shaft, i.e., on that glass surface of the cooling water jacket which is in contact with the gas or gas mixture to be irradiated. Suitable polymers which are clear at the operating temperature and therefore light-permeable are commercially available.

The invention also relates to the use of polyfluorinated and perfluorinated polymer coatings, especially in the form of PTFE perfluoropropylene shrink tubing, to protect glass apparatus against attack by hydrogen fluoride.

Photochemical processes in which hydrogen fluoride is used as reactant or forms—often only in traces—as a reaction product, are known. Published German patent application DE-OS 24 18 676 discloses the production of trifluoroacetyl chloride by photochemical oxidation of 1,1,1-trifluoro-2,2-difluoroethane with oxygen in the presence or absence of chlorine. Gas-phase processes for the production of halogenated acid chlorides are disclosed in U.S. Pat. Nos. 5,569,782 and 5,545,298. Disclosed is the oxidation of hydrogen-containing chlorofluoroalkanes in the presence of chlorine under irradiation with certain wavelengths of UV light ($\lambda >= 280$ nm, for example through borosilicate glass or irradiation in the absence of chlorine through quartz glass). A photochemical liquid-phase process is described in U.S. Pat. No. 5,259,938. In that process also, light of the above-mentioned wavelength is radiated. The photochemical production of acid fluorides is disclosed, for example, in the International Patent Application No. 96/29298. In addition to the production of carboxylic acid derivatives, other processes are known wherein hydrogen fluoride is used or released by photochemical induction. In the publication, "Programme and Abstracts" of the "15th International Symposium on Fluorine Chemistry," The University of British Columbia, Vancouver, Canada, Aug. 2–7 1997, Abstract P(2) 148, a process is described by Mitsuo Kurumaya, Tsunetoshi Honda and Tatsui Nishiyama for the production of aromatic compounds fluorinated in the nucleus. Amino aromatic compounds are diazotized in a solution of hydrogen fluoride and pyridine, and this is followed by a photochemically induced fluorodediazonation. The corresponding aromatic compounds fluorinated in the nucleus are then formed in a good yield. In this manner the authors produced various kinds of multisubstituted fluoroaromatic compounds which can be used as pharmaceutical and liquid crystal intermediates. HF can also form as a byproduct in the photochlorination of fluorine-containing haloalkanes or haloalkenes.

According to the invention, the use of a covering of polyfluorinated and perfluorinated polymers, especially polytetrafluoroethylene, perfluoropropylene, and mixtures and copolymers thereof, preferably in the form of shrink tubing, is appropriate for the protection of glass apparatus against the action of hydrogen fluoride generally in photochemical reactions in which hydrogen fluoride is used or forms. Also usable, for example, are polymers which comprise or consist of perfluoroalkoxy polymers (PFA) or polyvinylidene fluoride or mixtures thereof. Shrink tubing of copolymers of polytetrafluoroethylene and perfluoropropylene are especially well suited, such as TEFLON-FE® made by Technoplast. Advantageously, irradiation apparatus will have a shaft in which the radiator is disposed (immersion shaft reactors). Especially suitable for use are radiation apparatus which have a protective covering in the form of a shrink tubing of a polytetrafluoroethylene-polyperfluoropropylene, which is drawn onto the glass casing of the radiator in the immersion shaft.

Polyfluorinated and perfluorinated HF-resistant coverings or apparatus parts constructed from them, especially those composed of polytetrafluoroethylene and/or polyperfluoropropylene, are usable both for gas phase reactions and for liquid phase reactions. For example, the covering can be used in order to provide protection against the effects of hydrogen fluoride on glass apparatus involved in the production of acid fluorides, acid chlorides and aromatic compounds fluorinated in the nucleus, or in photochlorinations as described further above.

It is an advantage of the invention that even after months of use, no etching due to the effect of hydrogen fluoride can be detected on the glass apparatus. Irradiation through the covering is possible; even in long-term tests, no turbidity has been observed in the shrink tubing of PTFE-polyperfluoropropylene which was used.

The following examples are intended to further explain the invention without limiting its scope. The procedure is performed with all the safety precautions necessary when working with molecular oxygen. In the use of PTFE or other coverings, static electric charges can develop, which can be carried off by grounding, for example by a metal mesh.

EXAMPLES

Examples 1 to 4

Preparation of trifluoroacetyl fluoride from 2-chloro-1,1,1,2-tetrafluoroethane (124) with Hg immersion radiators
Lamps: Commercially available immersion radiators made by Heraeus Noblelight
Immersion radiators used:

Example 1: TQ 718 undoped

Example 2: TQ 718 doped with cadmium

Example 3: TQ 718 undoped

Example 4: TQ 718 undoped
Construction and Procedure

Example 1

Undoped Radiator, Borosilicate Glass

Into an approximately 900 ml immersion shaft photoreactor with cooling finger insert for immersion lamps of Duran 50$^R$(water-cooled), 101.3 g (0.74 mole) of 124, 15.1 g (0.47 mole) of oxygen and 5.2 g (0.07 mole) of chlorine were fed. All 3 substances were mixed ahead of the reactor and introduced together in gaseous form. Before the test the immersion lamp was allowed to warm up for 15 minutes, because only then is its full intensity reached. During this period the reactor was flushed with nitrogen. During the 30-minute reaction the temperature was 80° C. In this test a conversion of 85.46% was achieved, with a selectivity of 99.90% with respect to the trifluoroacetyl fluoride that was formed. Traces of TFAC. were detected in the exhaust gas.
Analysis The exhaust gas from the reactor was investigated by gas chromatography; identification of the substances was performed with GC-MS.

Example 2

Cadmium Iodide-doped Radiator, Borosilicate Glass

| Procedure: | As in Example 1 |
|---|---|
| Charge: | 105.4 g (0.77 mole) 124, 14.4 g (0.45 mole) oxygen, 5.1 g (0.07 mole) chlorine |
| Reaction temperature: | 0° C. |
| Conversion: | 93.09% |
| Selectivity: | 98.03% |

Construction and Procedure

Example 3

Undoped Radiator, Quartz Glass

Into an immersion shaft photoreactor with a capacity of about 900 ml, with cooling finger insert for immersion lamps of quartz (water-cooled), 69.2 g (0.51 mole) of 124, 10.0 g (0.31 mole) of oxygen and 3.2 g (0.05 mole) of chlorine were introduced. All 3 substances were mixed ahead of the reactor and introduced together in gaseous form. Before the test the immersion lamp was allowed to warm up for 15 minutes, because only then is its full intensity reached. During this period the reactor was flushed with nitrogen. During the 20-minute reaction the temperature was 115° C. In this test a conversion of 97.75% was achieved, with a selectivity of 91.38% with respect to the trifluoroacetyl fluoride that was formed. Traces of trifluoroacetyl chloride were detected in the exhaust gas.

Example 4

Undoped Radiator, Quartz Glass, Chlorine-free

| Procedure: | Like Example 3, immersion shaft photoreactor with a quartz cooling finger insert |
|---|---|
| Charge: | 109.8 g (0.80 mole) of 124, 15.2 g (0.48 mole) of oxygen without chlorine. |
| Reaction temperature: | 135° C. |
| Conversion: | 92.13% |
| Selectivity: | 90.85% |

Example 5

Preparation of trifluoroacetyl fluoride from 2-chloro-1,1,1,2-tetrafluorethane with fluorescent lamps as radiation source

| Charge: | 118.07 g of 124 = 0.91 mole |
|---|---|
| | 19.84 g of $O_2$ = 0.62 mole |
| | 9.93 g $Cl_2$ = 0.14 mole |
| Lamps: | 3 × 40 watt UV lamps from Philips |
| Type: | Cleo Performance R-UVA 40 W |
| Length: | 600 mm |

Consturction and Procedure

Into a 4.3-liter photoreactor (diam. 100 mm, wall thickness 2 mm) of Duran 50, a mixture of 118.07 g (0.91 mole)

124, 19.84 g (0.62 mole) oxygen and 9.93 g (0.14 mole) chlorine was introduced in gaseous form.

The reactor temperature during the 30-minute reaction was 41 to 46° C. Irradiation was performed with 3 commercial Philips UV fluorescent lamps equipped with a reflective covering on one side in order to increase the radiation yield (lamps arranged cylindrically around the reactor).

The conversion of the reaction was 65.17%, the selectivity with respect to the TFAF formed was 99.88%. In the gas chromatography traces of trifluoroacetyl chloride could also be detected.

Analysis

Analysis of samples of the reactor exhaust gas was performed by GC, the identification of the substances by GC-MS.

Example 6

Preparation of chlorodifluoroacetyl fluoride from 1,2-dichloro-1,1,2-trifluoroethane (123a) in Duran glass.

| Charge: | 80.10 g 123a = 0.53 mole |
| --- | --- |
| | 10.60 g $O_2$ = 0.33 mole |
| | 3.90 g $Cl_2$ = 0.06 mole |

Construction and Procedure

Oxygen, chlorine and 123a were passed through a 4.3 liter photoreactor of Duran 50 (reactor construction as in Example 5). Oxygen and chlorine were premixed and afterward added to the 123a in the preliminary evaporator which was heated to 100° C. The metering of the 123a into the preliminary evaporator was performed with a diaphragm pump with a coolable head.

The irradiation was performed with Philips regular commercial fluorescent lamps which are coated on one side with a reflector covering in order to increase the radiation output. The exact designation is Cleo Performance R-UVA 40 W. The nominal power of the lamps is 40 watts.

Duration of Test: 15 Minutes

The 123a is evaporated and passed through the reactor in admixture with the other reactants. Following the reactor there are two cooling traps with a methanol/$CO_2$ mixture in order for collecting the chlorodifluoroacetyl fluoride produced.

The reactor temperature amounted to up to 46° C., and iradiation was performed with 2×40 watts.

The conversion was 30.66%, the selectivity with respect to the CDFAF that was formed was 93.41%.

Analysis

The samples were investigated by gas chromatography; the identification of the substances was performed by GC-MS.

Example 7

Production of trifluoroacetyl fluoride from R 124 with a modified reactor.

Apparatus:

A photoreactor with a reactor capacity of 900 ml was used. It had an immersion shaft with a water-cooled finger to accommodate the radiator. A shrink tubing of TEFLON-FEP[R] made by Technoplast was used to cover the surface of the cooling finger, made of Duran 50 glass, of the immersion shaft that was in contact with the gas being irradiated. The lamp had a power of 700 W (TQ 718 Heraeus, undoped radiator).

Procedure:

A mixture of 51.3 g (0.37 mole) of 124, 6 g (0.19 mole) of oxygen and about 2.5 g (0.03 mole) of chlorine was passed through the reactor for a period of 15 minutes (internal temperature: 85° C.). No alteration of the shrink tubing (turbidity or yellowing) was observed. The conversion was 94.1%; the selectivity 99.6%.

Even throughout a long test period no alteration of the shrink tubing was observed.

Example 8

Testing the suitability of shrink tubing of polytetrafluoroethylene (PTFE) and perfluoroalkoxy polymers (PFA)

Procedure:

A PTFE-PFA shrink tubing, made by DuPont, was drawn onto an immersion shaft of Duran 50® and irradiated for 2 days with a Heraeus radiator. No formation of turbidity was observed, instead the tubing remained clear. This shows that PTFE-PFA polymers are very suitable for use in the manufacture of irradiating apparatus or shrink tubing for use in irradiation processes (despite the oxygen content in the polymer).

What is claimed is:

1. A process for producing $CF_3C(O)F$ comprising the step of photochemically oxidizing $CF_3CHClF$, with oxygen in the gaseous phase.

2. A process according to claim 1, wherein said oxidizing step is carried out in the presence of elemental chlorine.

3. A process according to claim 2, wherein the $CF_3CHClF$, the oxygen and the chlorine are subjected to activating irradiation with light having a wavelength λ of greater than or equal to 280 nm.

4. A process according to claim 1, wherein said oxidizing step is carried out in a flow-through reactor.

5. A process according to claim 4, wherein $CF_3CHClF$, oxygen and optionally chlorine are continuously introduced into the flow-through reactor, and carboxylic acid fluoride is continuously withdrawn from the flow-through reactor.

6. A process according to claim 1, wherein said oxidizing step is carried out at a pressure of from 1 to 2 bar (absolute).

7. A process according to claim 1, wherein $CF_3CHClF$ and oxygen are supplied to said oxidizing step in a molar ratio of 1:0.1 to 1:1.5.

8. A process according to claim 2, wherein $CF_3CHClF$ and elemental chlorine are present in a molar ratio of 1:0.01 to 1:1.

9. A process according to claim 2, wherein the oxidizing step is performed by photochemical oxidation at a temperature of up to 200° C.

10. A process according to claim 4, wherein the flow-through reactor is operated so as to have an average residence time in the range from 0.01 to 30 minutes.

11. A process according to claim 1, wherein the photochemical oxidation is initiated by activation from fluorescent tubes which emit only (UV) light having a wavelength of at least 280 nm.

12. A process according to claim 1, wherein the photochemical oxidation is initiated by activating radiation from doped radiator.

13. A process for preparing $CF_3C(C)F$ according to claim 1, wherein the step of photochemically oxidizing $CF_3CHClF$ with oxygen in the gaseous phase is effected in the presence of elemental chlorine under the influence of activating radiation from a high-pressure mercury lamp doped with a metal iodide and at a temperature in the range from 30 to 90° C. in a flow-through reactor operated such that the reactor has a residence time in the range from 0.5 to 3.5 minutes; the $CF_3CHClF$ and oxygen being supplied to the oxidizing step in a molar ratio of 1:0.4 to 1:0.6; and the elemental chlorine being present in an amount sufficient to establish a molar ratio of $CF_3CHClF$ to elemental chlorine in the range from 1:0.05 to 1:0.2.

14. An apparatus for carrying out photochemical reaction of gaseous reactants, said apparatus comprising a container for receiving a reactant gas to be irradiated; a radiator disposed in a casing of glass which is in contact with the gas to be irradiated, and a radiation-permeable protective covering disposed on at least a portion of the surface of the glass casing, said protective covering comprising a shrink tubing composed of radiation-permeable polyfluorinated or perfluorinated polymer material drawn onto the glass casing.

15. An apparatus according to claim 14, wherein the protective covering on the glass casing is comprised of polytetrafluoroethylene, polyfluoropropylene or a mixture thereof.

16. A method of protecting a glass part of a photochemical reactor exposed to hydrogen fluoride consumed or produced in a photochemical reaction therein, said method comprising enclosing said glass part in a radiation-permeable shrink tubing of polyfluorinated or perfluorinated polymer material.

17. A method according to claim 16, wherein said polymer material is comprised of polytetrafluorethylene, perfluoropropylene or mixtures or copolymers thereof.

18. A method according to claim 16, wherein said photochemical reaction is selected from the group consisting of photochemical oxidation of hydrogen-containing halocarbon compounds, photochemical induced fluorodediazonation, and photochlorination.

* * * * *